(12) United States Patent
Jia et al.

(10) Patent No.: US 10,175,162 B2
(45) Date of Patent: Jan. 8, 2019

(54) PAPER SENSING AND ANALYTIC SERVICE WORKFLOW METHODS AND SYSTEMS

(71) Applicant: Xerox Corporation, Norwalk, CT (US)

(72) Inventors: Nancy Y. Jia, Webster, NY (US); Mandakini Kanungo, Webster, NY (US); Wei Hong, Amherst, MA (US); Jing Zhou, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 61 days.

(21) Appl. No.: 14/825,876

(22) Filed: Aug. 13, 2015

(65) Prior Publication Data

US 2016/0054229 A1 Feb. 25, 2016

Related U.S. Application Data

(60) Provisional application No. 62/041,191, filed on Aug. 25, 2014.

(51) Int. Cl.
| | |
|---|---|
| *G01N 31/22* | (2006.01) |
| *G01N 21/25* | (2006.01) |
| *G01N 21/78* | (2006.01) |
| *G16H 10/60* | (2018.01) |
| *G01N 21/84* | (2006.01) |
| *G06F 19/00* | (2018.01) |
| *G01N 21/77* | (2006.01) |

(52) U.S. Cl.
CPC ......... *G01N 21/253* (2013.01); *G01N 21/251* (2013.01); *G01N 21/78* (2013.01); *G01N 21/8483* (2013.01); *G06F 19/00* (2013.01); *G16H 10/60* (2018.01); *G01N 2021/7759* (2013.01)

(58) Field of Classification Search
CPC .............. G01N 21/78; G01N 21/8483; G01N 2021/7759; G06F 19/322
See application file for complete search history.

(56) References Cited

U.S. PATENT DOCUMENTS

| | | |
|---|---|---|
| 7,454,880 B1 | 11/2008 | Austin et al. |
| 7,969,624 B2 | 6/2011 | Mestha et al. |
| 8,249,879 B2 | 8/2012 | Bangalore et al. |
| 8,377,710 B2 | 2/2013 | Whitesides et al. |
| 8,628,729 B2 | 1/2014 | Carrilho et al. |

(Continued)

FOREIGN PATENT DOCUMENTS

WO WO-2014197604 A2 * 12/2014 ............ H04W 4/006

OTHER PUBLICATIONS

Martinez et al,"Simple Telemedicine for Developing Regions: Camera phones and paper-based microfluidic devices for Real-Time, Off-Site Diagnosis" Anal. Chem, 2008, 80, p. 3699-3707.*

*Primary Examiner* — Dennis White
(74) *Attorney, Agent, or Firm* — Fay Sharpe LLP (57) ABSTRACT

This disclosure provides a workflow method and system associated with a paper-based sensor. Specifically, provided is a paper-based sensor workflow including printing of customized security sensing information and bio-reagents to produce a paper-based sensor, applying a test material, such as, but not limited to, blood, to the paper-based sensor, capturing an image of the paper-based sensor and performing a colorimetric process; and performing one or more analytics to produce results associated with the test material.

16 Claims, 9 Drawing Sheets

(56) References Cited

U.S. PATENT DOCUMENTS

| | | |
|---|---|---|
| 8,730,460 B2 | 5/2014 | Yan et al. |
| 8,821,810 B2 | 9/2014 | Whitesides et al. |
| 2007/0061393 A1 | 3/2007 | Moore |
| 2009/0209904 A1* | 8/2009 | Peeters ................ A61B 5/0002 604/66 |
| 2009/0298191 A1* | 12/2009 | Whitesides .......... G01N 33/523 436/164 |
| 2011/0111517 A1 | 5/2011 | Siegel et al. |
| 2011/0123398 A1* | 5/2011 | Carrilho ................ B01L 3/5023 422/68.1 |
| 2012/0053930 A1 | 3/2012 | Bangalore et al. |
| 2012/0181184 A1 | 7/2012 | Whitesides et al. |
| 2012/0198685 A1 | 8/2012 | Bernardina Junior |
| 2012/0257188 A1 | 10/2012 | Yan et al. |
| 2013/0034869 A1 | 2/2013 | Whitesides et al. |
| 2013/0084630 A1 | 4/2013 | Rolland et al. |
| 2015/0301031 A1* | 10/2015 | Zin .................. G01N 33/48792 436/164 |

* cited by examiner

| CLINICALLY RELEVANT CONCENTRATIONS: | | |
|---|---|---|
| µg/µL | mg/dL | |
| < 2 | < 200 | NORMAL |
| 2.0 - 2.4 | 200 - 240 | BORDERLINE HIGH |
| > 2.4 | > 240 | UNHEALTHY |

FIG. 14

PAPER SENSING AND ANALYTIC SERVICE WORKFLOW METHODS AND SYSTEMS

This application claims priority to U.S. Provisional Patent Application No. 62/041,191, filed Aug. 25, 2014, by Nancy Jia et al. and entitled "PAPER SENSING AND ANALYTIC SERVICE WORKFLOW METHODS AND SYSTEMS" and is incorporated herein by reference in its entirety.

CROSS REFERENCE TO RELATED PATENTS AND APPLICATIONS

U.S. patent application Ser. No. 14/799,832, filed Jul. 15, 2015, by Hong et al. and entitled "DESIGN OF PAPER SENSOR";

U.S. patent application Ser. No. 14/799,969, filed Jul. 15, 2015, by Zhou et al., and entitled "ROBUST COLORIMETRIC PROCESSING METHOD FOR PAPER BASED SENSORS";

U.S. patent application Ser. No. 14/806,412, filed Jul. 22, 2015, by Zehler et al., and entitled "VENDOR EXCLUSIVITY SECURITY FEATURE FOR PAPER-BASED DIAGNOSTIC SOLUTION";

U.S. patent application Ser. No. 14/312,061, filed Jun. 23, 2014, by Zhou et al., and entitled "APPARATUS FOR FORMING HYDROPHOBIC STRUCTURES IN POROUS SUBSTRATES";

U.S. patent application Ser. No. 14/312,209, filed Jun. 23, 2014, by Zhou et al., and entitled "APPARATUS FOR PRODUCING PAPER-BASED CHEMICAL ASSAY DEVICES";

U.S. patent application Ser. No. 14/311,970, filed Jun. 23, 2014, by Beachner et al., and entitled "SYSTEM AND METHOD FOR FORMING BONDED SUBSTRATES";

U.S. patent application Ser. No. 14/311,909, filed Jun. 23, 2014, by O'Neil et al., and entitled "SYSTEM AND METHOD FOR FORMING HYDROPHOBIC STRUCTURES IN A POROUS SUBSTRATE", are incorporated herein by reference in their entirety.

BACKGROUND

Paper-based sensing (i.e. paper-based test devices) is an emerging technology that has advantages relative to traditional test strips in terms of cost and multiplexing. The concern of poor accuracy on paper-based sensors and paper test strips, due to the colorimetric measurement, has limited them from quantitative applications. In the existing test strip applications, a user has to manually compare resultant colors to a set of colors on a separate reference card. This is neither user friendly nor reliable. Recently some companies have developed phone 'apps' to automate the test strip reading process using a phone camera.

INCORPORATION BY REFERENCE

U.S. Pat. No. 8,377,710, issued Feb. 19, 2013, by Whitesides et al., and entitled "LATERAL FLOW AND FLOW-THROUGH BIOASSAY DEVICES BASED ON PATTERNED POROUS MEDIA, METHODS OF MAKING SAME, AND METHODS OF USING SAME";

U.S. Pat. No. 8,628,729, Issued Jan. 14, 2014, by Carrilho et al., and entitled "THREE-DIMENSIONAL MICROFLUIDIC DEVICES";

U.S. Pat. No. 8,249,879, Issued Aug. 21, 2012, by Bangalore et al., and entitled "SYSTEM AND METHOD OF PROVIDING A SPOKEN DIALOG INTERFACE TO A WEBSITE";

U.S. Pat. No. 8,730,460, Issued May 20, 2014, by Yan et al., and entitled "PAPER BASED SPECTROPHOTOMETRIC DETECTION OF BLOOD HEMOGLOBIN CONCENTRATION";

U.S. Pat. No. 8,821,810, Issued Sep. 2, 2014, by Whitesides et al., and entitled "DEVICES AND METHODS FOR MULTIPLEXED ASSAYS";

U.S. Patent Application Publication No. 2011/0111517, published May 12, 2011, by Siegel et al., and entitled "PAPER-BASED MICROFLUIDIC SYSTEMS";

U.S. Patent Application Publication No. 2012/0181184, published Jul. 19, 2011, by Whitesides et al., and entitled "MICROFLUIDIC, ELECTROCHEMICAL DEVICES";

U.S. Patent Application Publication No. 2012/0198685, published Aug. 9, 2012, by Bernardina Junior, and entitled "METHOD TO PRODUCE AN ELECTRODE WITH A LOW LEVEL OF HYDROGEN AND LOW ABSORPTION OF MOISTURE"; and U.S. Patent Application Publication No. 2013/0084630, published Apr. 4, 2013, by Rolland et al., and entitled "QUANTITATIVE MICROFLUIDIC DEVICES", are incorporated herein by reference in their entirety.

BRIEF DESCRIPTION

In one embodiment of this disclosure, described is a paper-based sensor method comprising: applying a test sample of a substance to a paper-based sensor, the paper-based sensor reacting to the test sample to generate one or more color indicators; capturing an image of the paper-based sensor after the test sample is applied to the paper-based sensor; and performing colorimetric image processing of the captured image of the paper-based sensor to determine one or more colorimetric properties associated with the paper-based sensor, wherein the colorimetric properties indicating one or more attributes associated with the test sample.

In another embodiment of this disclosure, described is a paper-based sensor processing system comprising: a processor and associated memory configured to receive a captured image of a paper-based sensor after a test sample is applied to the paper-based sensor. The processor and associated memory configured to execute instructions to perform a method comprising: performing colorimetric image processing of the captured image of the paper-based sensor to determine one or more colorimetric properties associated with the paper-based sensor, wherein the colorimetric properties indicating one or more attributes associated with the test sample.

In still another embodiment of this disclosure, described is a computer program product comprising: a non-transitory computer-usable data carrier storing instructions that, when executed by a computer, cause the computer to perform a method comprising: performing colorimetric image processing of a captured image of a paper-based sensor after a test sample is applied to the paper-based sensor. The colorimetric image processing determining one or more colorimetric properties associated with the paper-based sensor and the colorimetric properties indicating one or more attributes associated with the test sample.

DETAILED DESCRIPTION

As discussed in the background, paper-based sensing is an emerging technology that has advantages relative to traditional test strip in terms of disruptive cost and multiplexing. The concern of poor accuracy associated with a paper-based sensor and paper test strip due to colorimetric measurements has limited them from quantitative applications. For an existing test strip application, a user has to manually compare resultant color to a set of color reference cards. This is neither user friendly nor reliable. Recently some companies have attempted to develop phone 'apps' to automate the test strip reading process using a phone camera.

This disclosure provides a novel end-to-end workflow/solution to enable real-time patient or user health condition monitoring/feedback. User monitoring comprises health condition monitoring including home care, self-administered monitoring, health/wellness screening, risk assessment, etc. The disclosed work flow/system solution includes printing of customized security and sensing information, printing of bio-reagents applications, a colorimetric process method, and a software platform. This end-to-end workflow provides robust and accurate result reading and patient feedback using paper-based sensors with various different cameras and various different lighting conditions. Unlike a test strip application where a color reference card is required, the disclosed method and system prints reference color(s) along with a hydrophobic channel(s) on a paper sensor substrate during a device fabrication process and provides the users real-time quantitative results.

Figure 1:
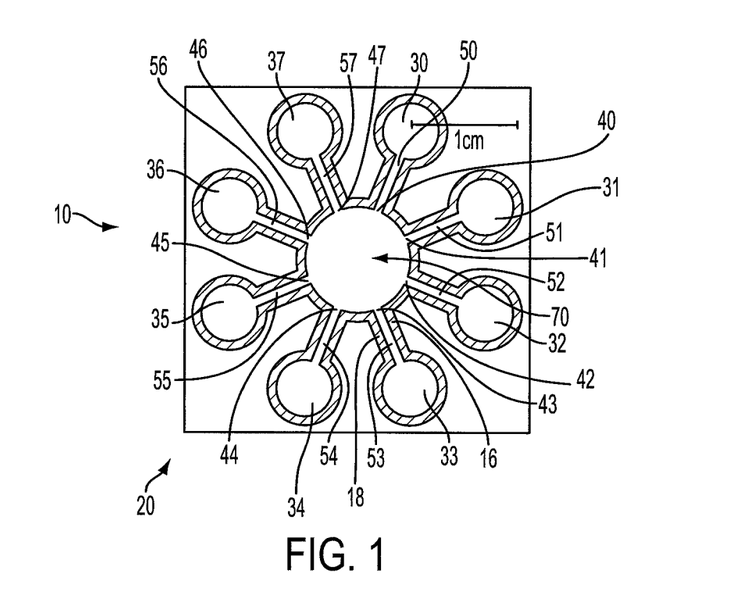
FIG. 1 represents one type of a paper-based sensor or test device.
Figure 2:
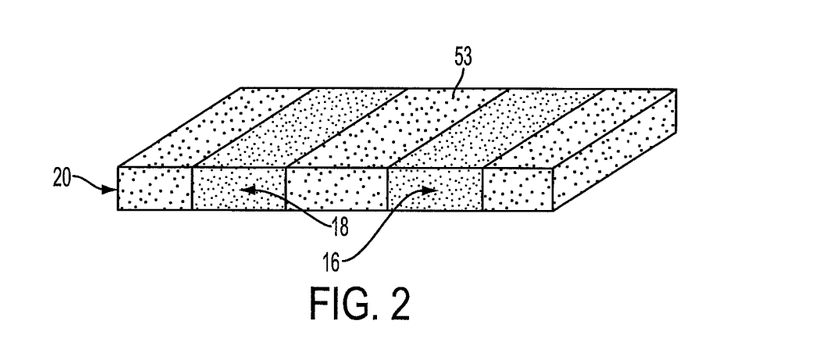
FIG. 2 represents an enlarged partial section of the paper-based sensor of FIG. 1.

A paper-based sensor or paper-based device 10, as shown in FIG. 1, is a small biomedical device made of paper, wax, and reagents that can analyze bioassays in test fluids or test liquids such as blood, urine and saliva. The hydrophobic barrier walls 16, 18 are made of wax and can penetrate through the entire thickness of the paper 20 (i.e. hydrophilic matrix) to create and separate (i.e. divide) various fluidic components such as a series of test regions 30, 31, 32, 33, 34, 35, 36, 37, fluid entrances 40, 41, 42, 43, 44, 45, 46, 47, transport channels 50, 51, 52, 53, 54, 55, 56, 57, and mixers or reagents. The transport channels 50-57, can be hydrophobic (i.e. wax) channels extending through the hydrophilic matrix paper 20. Various reagents with various and/or different concentrations can be pre-deposited on the test regions 30-37. During the diagnostic process, capillary forces pull portions of the test fluid 70 to associated multiple test regions 30-37 and upon contacting the pre-deposited reagents, react with the respective portions of test fluid 70. A signal, color change, or color shade is generated if a specific analyte is present in the test fluid 70; for example, a color change or shade develops where the color density varies based on the concentration of the analyte. The color change or shade can be captured and recorded by an imaging device such as a smart phone or camera phone and can then be processed by an algorithm to calculate the concentration of each analyte based on a calibration curve or color scale of the device. The diagnostic results and/or raw data (if the image processing and diagnostic analysis is done on the server side) can be uploaded to a data server where the user's or patient's history can be stored for inquiry and advanced data analytics can be performed to detect and prevent adverse health conditions/diseases. It is to be appreciated that the user's data analytics can be used for trend monitoring, health screening, risk assessment, et al; the results of which can include non-adverse health conditions.

Paper based sensors have several advantages over traditional test strips. Test strips are simplex (one test per test strip), while paper sensors can be multiplex (multiple tests on one test device). Traditional test strips require relatively more test fluid than paper sensors. Test strips are fabricated by analog technology, while paper sensors can be digitally printed and quantitatively analyzed which enables greater customization and personalization.

Traditional test strips require users to manually measure a color with a color reference card, which can be unreliable and limits their application in quantitative measurement. New software has been developed to automate the test strip measurement process with a phone camera. However, a color reference card is still required to calibrate the camera RGB (Red-Green-Blue) space and the total intensity is used for concentration measurement.

Use of paper based sensors is an emerging technology that provides advantages over traditional test strips in terms of reducing costs and multiplexing. Current paper based sensors require a user to provide a certain amount of test liquid (blood, urine, etc.) to ensure the accuracy of the test. The level of multiplexing is typically limited by the printing resolution and straightness of printed wax vertical walls/barriers. Additionally, the current method of reading colorimetric information uses either a separate manual reference card or uses a mobile application available in the market that can suffer from the variability for individual reading devices (camera, illumination, light direction, surrounding light conditions, etc.). It is important to develop novel designs for paper based sensors that can achieve a higher level of multiplexing than the current devices available in the market, and can provide higher readout accuracy regardless of the variation from individual reading devices.

The present disclosure provides an overall workflow associated with a paper sensor device, and method of use thereof, including the printing of customized security information and device condition indicators, printing of bio-reagents, a colorimetric process method, and a software platform.

In one exemplary embodiment (FIG. 3), a paper sensor device 200 can include the following components: a structural forming layer 216, an optional filter membrane layer 212, and at least two laminating layers 218, 220. The structure forming layer 216 can include a channel structural area 224, a test area 210, a calibration reference area 226, and an auxiliary information area 228.

Figure 3:
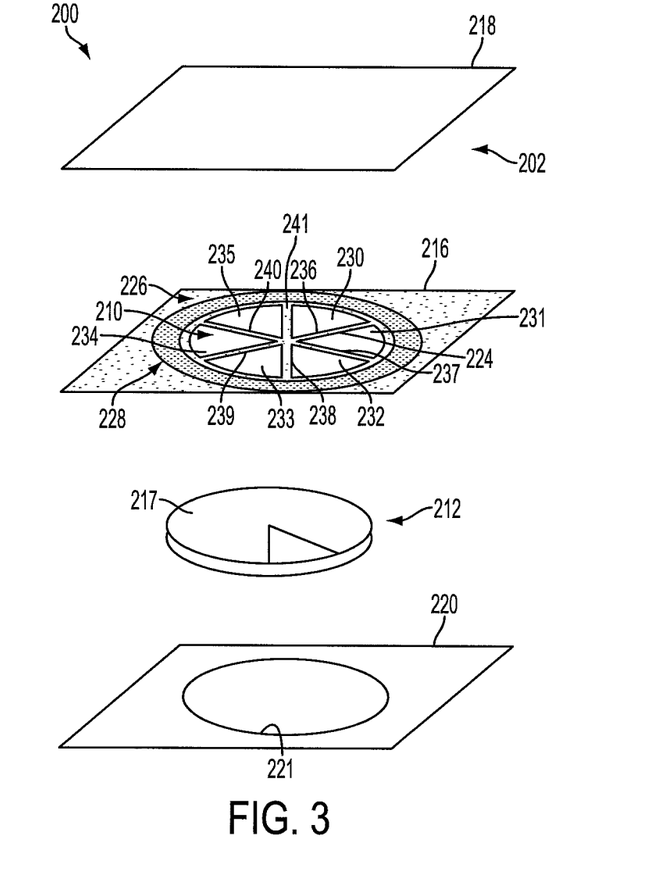
FIG. 3 is an exploded view of a paper-based sensor according to the present disclosure.

The test area or test zone 210 can include 1 to n (n>=2) individual segmented test zones 230, 231, 232, 233, 234, 235. The segmented test zones 230-235 can be arranged in an axially symmetric or axially radiating manner. The total test area 210 is from about 25% to about 60%, and preferably at least 37.5% of the total device area 202. The minimum area of individual test zones 230-235 is 5 mm². Comparing to the prior art devices (FIG. 1), the individual test zones 230-235, of the present disclosure, are at least three (3) times larger. Test zones 230-235 are surrounded and divided by wax ink barrier walls 236, 237, 238, 239, 240, 241 (i.e. solid ink barriers) with a wall width of about 100 um for maximizing the area of the test regions or zones 230-235 relative to a limited space or area for the device 202. It is to be appreciated that a majority of the volume of a test sample is utilized and reaches, i.e. reacts with, the reagents in each of the test zones 230-235.

One exemplary test panel can include respective reagents in test zones 230-235 for measuring levels of triglyceride, total cholesterol, HDL (i.e. three individual test zones). Another exemplary test panel can include respective reagents in test zones for measuring lipid panel, i.e. levels of triglyceride, total cholesterol, HDL, Hemoglobin A1C (HbA1C), glucose (i.e. five individual test zones). In the aforementioned manner, each test zone 230-235 has a different reagent. It is to be appreciated that each test zone can alternatively have a different concentration of the same reagent to measure different levels of a single bioassay.

Auxiliary information or identifying text (for example, GL represents glucose, TG represents triglyceride, A1C represents hemoglobin, HDL represents HDL cholesterol, and TC represents total cholesterol) labels the type of test in each test zone 230-235 and can be printed outside and adjacent to the test zones or regions (i.e. reference regions).

The optional filter membrane layer 212 can have a separation membrane 217 (i.e. plasma separation) that covers the total test area 210. Alternatively the optional filter membrane layer 212 can have a partial separation membrane and partial "other materials" (i.e. paper) to enable the controlled flow of the test sample. The plasma separation membrane 217 can include a series of pores on the top surface as well as the bottom surface. The series of pores can have a pore sized gradient between the top surface and the bottom surface. In particular, the pore size on the top surface can be greater than the pore size on the bottom surface.

Membrane layer 212 and structural forming layer 216 can be sandwiched between laminate film layers 218, 220. A hole 221 that is smaller than the size of the membrane 217 can be cut in the bottom lamination layer 220 at the backside of the device (FIG. 3). The plasma separation membrane 217 can be visible on the backside of the device 200 when the device 200 is in the assembled arrangement.

The present disclosure proposes a design of a biomedical paper sensor 200 which can determine the concentration of biological materials in fluids such as blood, urine, and saliva. The sensor 200 can contain axially radiating and/or axially symmetric test zones 230-235 arranged similar to slices of a pie (for example) divided by wax ink barriers 236-241 formed by a process that produces thin walls. Each test zone 230-235 can contain a unique test reagent and can be identified by printed text (not shown) in area 228. The region 226 of the device outside of the test zone 230-235 can be printed with a uniform reference color. Additionally the color of the wax wall can also serve as a reference color when it is not clear. Benefits of the sensor 200 include increased accuracy in the measurement of the concentration of biological materials due to the larger area of the test zones. Benefits also include the integration of the reference or calibration color 226 into the sensor 200 which simplifies a visual calibration review, check, or comparison needed for quantification of the concentration of the test fluid (i.e. test sample).

Figure 4:
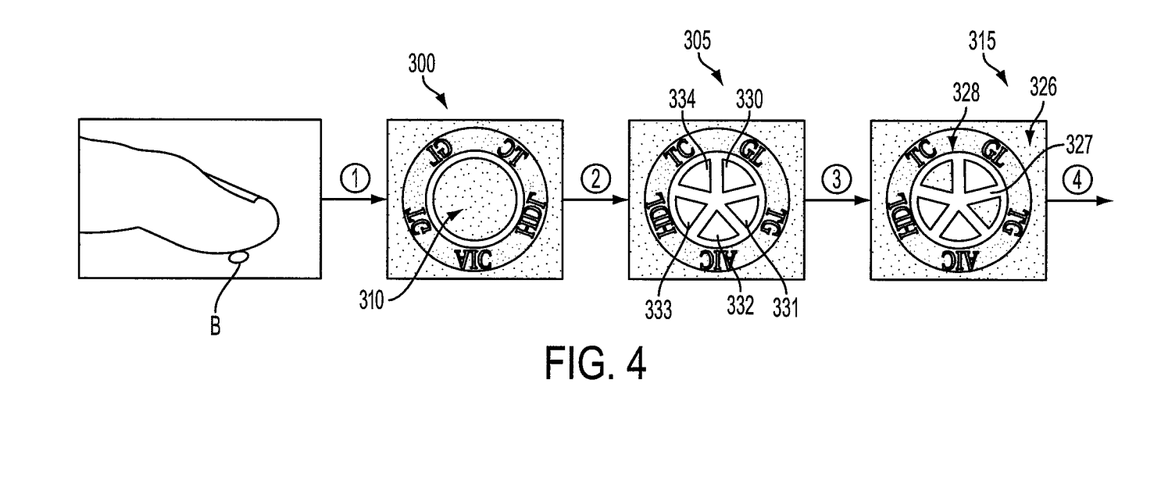
FIG. 4 shows the processing of a blood sample by an exemplary paper sensor device according to an exemplary embodiment of this disclosure.

FIG. 4 illustrates the processing of a blood sample by an exemplary paper sensor device according to an exemplary embodiment of this disclosure. FIG. 4 displays a method of using the paper sensor device 300. A blood sample B is taken from a patient/testing target and "sucked" into the bottom of the device, i.e. the test area 310, of the paper sensor 300 (step 1). The paper sensor 300 can be turned right side up wherein the blood sample processing can be viewed (step 2). The assay development 305 proceeds in which the blood sample B makes contact with the respective reagents in the test zones 330, 331, 332, 333, 334 (step 3). After the sample has reacted to the reagents, the developed assay 315 is subsequently formed (step 4). It is to be appreciated that the paper sensor device 300 performs sample collection; sample processing; assay development 305; and, assay readout 315. The sensor 300 also incorporates a calibration reference area 326, 327 and an auxiliary information area 328. Areas 327, 327, and 328 can be used as reference color areas or contrast color areas. Areas 327 and 328 can be any color to provide contrast (black, color, contrast color, etc.) between areas 330-334 and reference areas 326, 327, and 328. It is to be appreciated that the calibration reference area 326 can be separated into multiple sub-areas including separate reference colors associated with each sub-area (not shown). The multiple color reference areas enable use of reagents with different dye colors in test zones 330-334. Alternatively, the reference region can include a first calibration color area including a first predeterminable color for comparing to one or more of the axial test zones. The reference region can further include a second calibration color area including a second predeterminable color for comparing to one or more of the axial test zones. The first and second calibration color areas can each include first and second predeterminable colors, respectively, for comparing to one or more of the axial test zones to report or indicate the concentration of at least two test substance analytes based on the calibrated reading in each test area. In one embodiment, the substrate region 328 can include a contrasting color to distinguish between the test zones 330-334 and the calibration color area 326. Although not shown in FIG. 4, the triglyceride paper sensor 300 can display a gradient of color change in the test zones 330-334 due to different concentrations of the triglyceride. The color change or color shade of test zones 330-334 can be compared to the reference color 326 (i.e. magenta). It is to be appreciated that the color change or color density represents the concentration of triglyceride (for example) from associated test zones 330, 331, 332, 333, 334, and can include concentrations of 100, 150, 200, 250, 300 mg/dL, respectively.

In the example shown in FIG. 4, the paper sensor 300 can display a gradient of color change in the test zones 330-334 due to different types of reagents, and/or different concentrations of a reagent, that can measure different levels of a bioassay. It is to be appreciated, that each type of analyte (GL, TG, HbA1C, HDL, TC) can use a different reagent, and each analyte/reagent pair can have an associated calibration curve for color reference. Additionally, for a single analyte assay determination, color change in the test zones 330-334 can be due to different concentrations of the same reagent in each test zone. The test zones 330-334 can be compared to the calibration or reference color 326 (i.e. magenta). In this manner, the biomedical paper sensor 300 is used for determining a concentration of biological materials contained in fluids (i.e. blood sample). The reference color or region 326 can include one or more calibration color areas having predeterminable colors for comparing to one or more of the test areas or zones, for reporting or indicating the concentration of test substance (analyte) based on calibrated reading in each test area. In one exemplary arrangement, the calibration color area can include multiple sections. Each section can have a distinct predeterminable color used for a specific analyte. For example, two calibration color sections can comprise one red section and one blue section. In one exemplary arrangement, the red section can be used to calibrate HbA1C and the blue section can be used to calibrate HDL.

Figure 5:
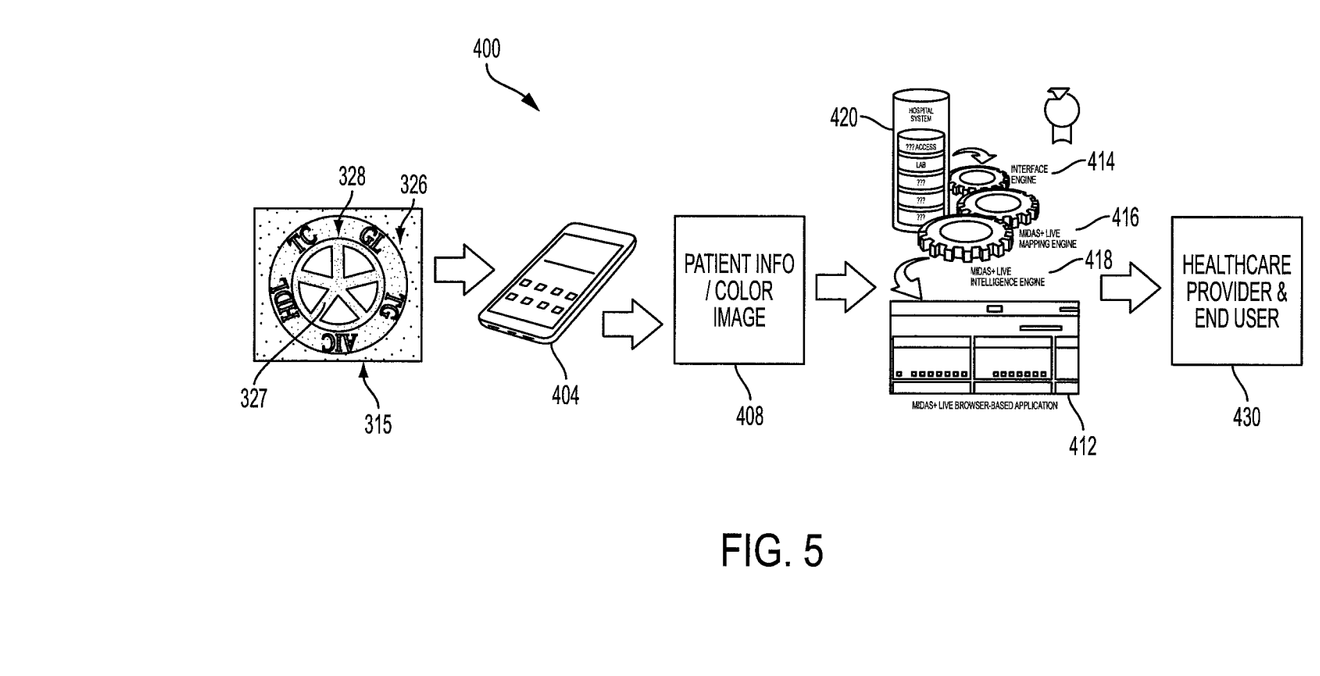
FIG. 5 is an exemplary embodiment of a Paper Sensing and Analytic Service (PSAS) workflow according to an exemplary embodiment of this disclosure.

FIG. 5 continues the PSAS workflow 400 that begins with the biomedical paper sensor 300 including a fluid sample collected, processed, developed, and the resulting assay 315 displayed. The assay development and display 315 can be photographed and uploaded to, for example, a cell phone 404. Once uploaded, the resultant assay 315 can be transmitted 408 to a browser based application 412 that includes an interface engine 414, mapping engine 416, and intelligence engine 418. The browser based application 412 can reside in a healthcare system database 420 that connects patient information/access, lab results, radiology, clinical, prescription. The assay results in the system database 420 can then be accessed by a healthcare provider and/or end user 430 via an interfaced computer network and utilizing any various programs to ensure protected and secure access.

Figure 6:
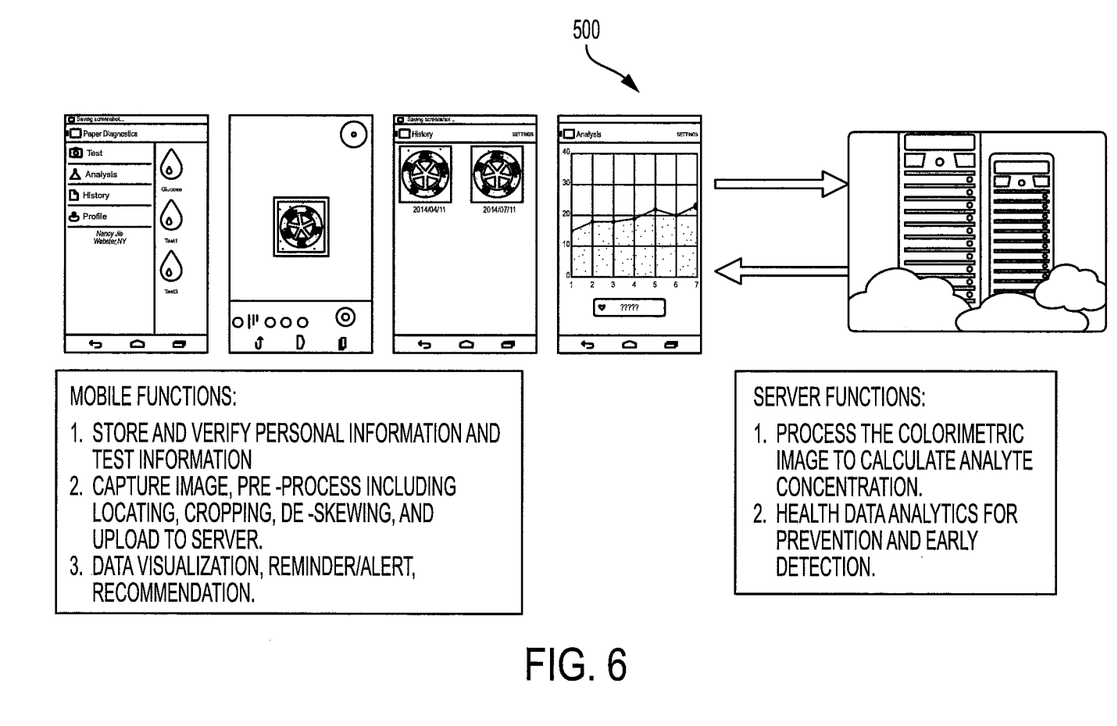
FIG. 6 is an exemplary platform for implementing a paper device sensor workflow according to this disclosure.

FIG. 6 illustrates an exemplary software platform 500 for implementing the paper device sensor workflow 400 according to this disclosure. As shown in FIG. 6, according to an exemplary embodiment a smart phone including a camera and sufficient cpu computing power can perform all or partial image processing/analytics associated with the captured image in the local computers or through a server. For example, all image processing, etc. is performed utilizing a camera phone where diagnostic results are generated by the camera phone, i.e. smart phone, and uploaded to a server. Also, the server function can be cloud based according to an exemplary embodiment. The mobile functions include storing and verifying personal information and test information. Further, the mobile functions can capture the image, preprocess the image including locating, cropping, de-skewing, and uploading to the server. The functions further include data visualization, calibration, reminders/alerts, and/or recommendations. The server functions include processing the colorimetric image to calculate analyte concentrations. This workflow allows the end users and/or care providers etc. to monitor health-conditions instantly form their own home, care facilities and elsewhere in a secure manner. As discussed, the health data analytics can be used for prevention and early detection of diseases and/or health problems.

Figure 7:
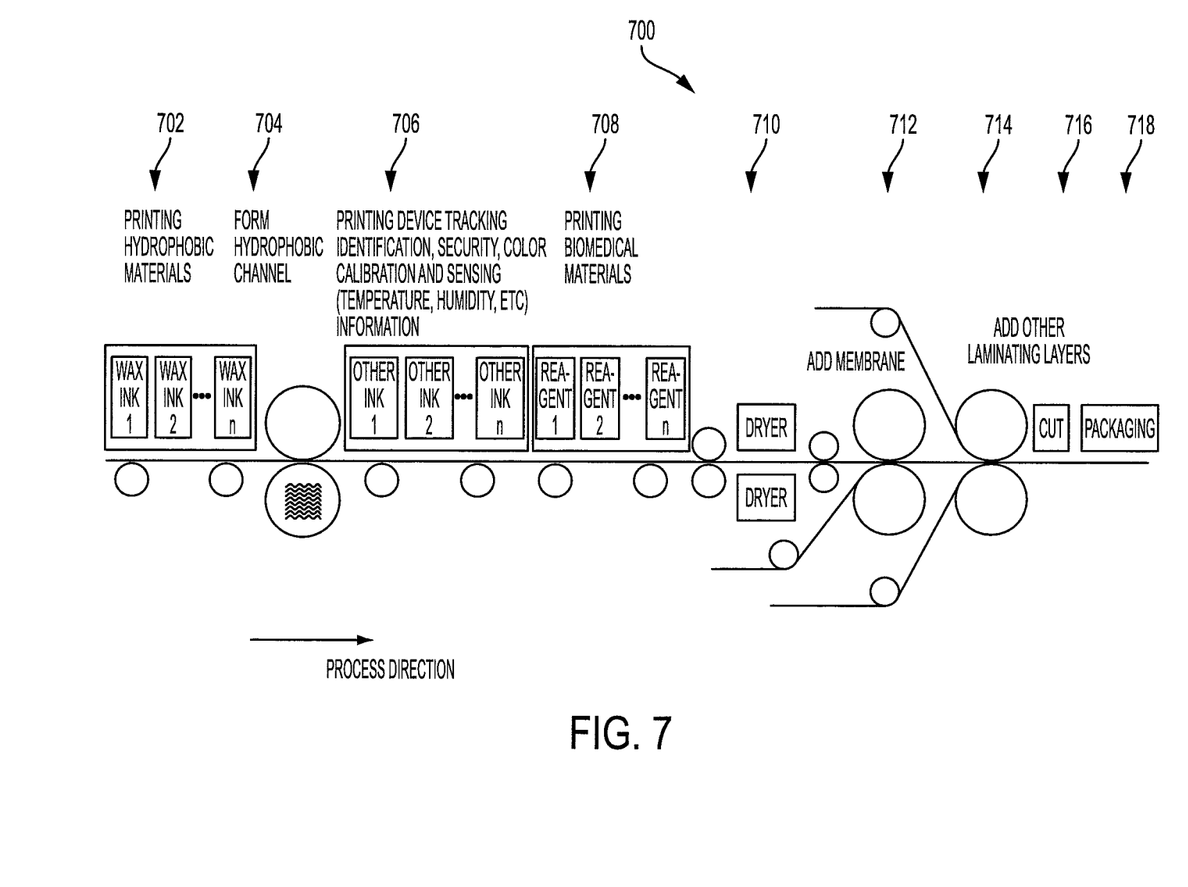
FIG. 7 shows an exemplary paper sensing device fabrication process according to this disclosure.

FIG. 7 illustrates a paper sensor device fabrication process/workflow 700. As shown in FIG. 7, the apparatus for fabricating the chemical assay devices includes a substrate transport configured to move a first hydrophilic substrate in a process direction, the process can include: a first print zone including at least one printhead to print solid/wax ink device structure (wells, channels etc.) 702; a structure formation unit to apply heat and pressure to enable wax ink to flow/penetrate through the paper substrate 704; print unique device tracking, identification, security and color calibration and device environmental or health condition indicators (temperature, relative humidity, etc.) 706 (alternately this might be printed at station 702); print biomedical materials 708; dry biomedical materials 710; cut filter membrane and add/align the material to the device structure 712; add other laminating layers and perform lamination 714; cut the devices to the desired shape and size 716; and package the product including assembled devices/testing strips, instructions, desiccant, etc. 718.

The paper device (testing strip) environmental or health conditions, such as the expiration status of the reagents, can be monitored via the color change of a printed sensor in the device (for example recording the history of temperature change or humidity change and send a warning signal if temperature or humidity exceed the normal ranges).

The patient's identification can be printed in addition to device information, to help the test management within a point-of-care environment. A patient who has to do multiple different diagnostic tests in a day can be confused and it is helpful for the patient to know which test needs to be performed on what time. Phone software can send a reminder to the patient and help the patient to identify the correct diagnostic device at specific schedules based on the security information on devices before test. The hidden security information will also help patients or health-care insurance providers to address any privacy concerns and detect illegal actions.

The patient's demographic information and health information can be printed in addition to device information to assist advanced diagnostic analysis. The current one-for-all diagnostic approach has limitations with respect to timely and accurate diagnosis because patients who have the same disease can be very different from each other. For example, a certain population may have higher risk and lower threshold for a particular analytic. These types of distinctions are particularly important for predictive analytics to improve personalized care and preventive care.

The security information is also used for data analytics. A large amount of diagnostic data from different patients over a long period of time is needed for building predictive modeling. For example, a two-year glucose history is usually tracked for estimating a diabetic's risk for kidney failure. The security information on paper-based diagnostic devices can ensure the privacy, accuracy and reliability of the diagnostic data before being sent to server. The historical data/truth curves can help to predict a patient's future conditions.

In addition, the information about the device manufacturer, manufacturing date, device category, device function, device tracking number, and target population can be printed on the paper-based diagnostic device and/or device packaging. The manufacturing information can be used to prevent counterfeits, protect the brand names, and provide traceability for accident investigations. The device information can be used to prevent fraud and errors where a diagnostic device associated with a first person does not become associated with a second person's identity. The manufacturing and device information together can be used to validate the device as all paper-based diagnostic devices have a limited shelf life.

Figure 8:
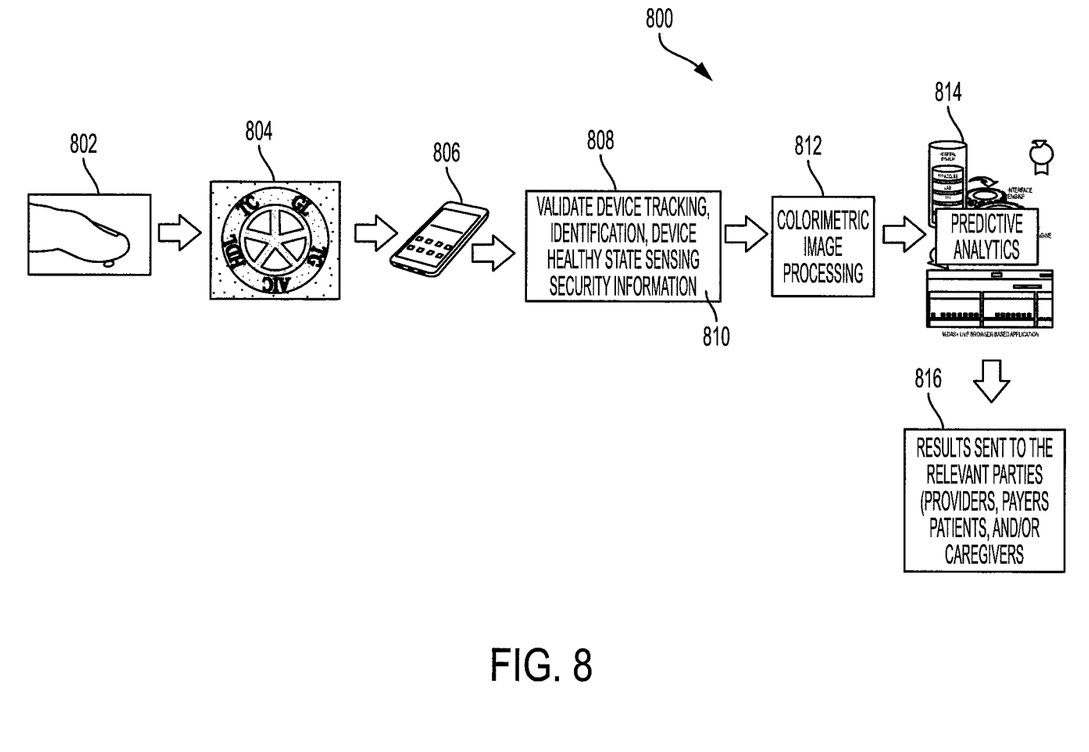
FIG. 8 is another exemplary embodiment of a PSAS workflow according to this disclosure.

With reference to FIG. 8, illustrated is another exemplary embodiment of a PSAS workflow 800 according to this disclosure. The PSAS 800 workflow can include the following functions: collect samples following the specific instructions 802; regents react with an analytic in the sensing device, causing the color changes 804; the color changes are captured by imaging device such as, but not limited to, a smart phone or any phone with a camera 806; wherein the device condition sensing includes a known indicator detecting whether the device is still fully functional (not expired) and whether the device is ready for image processing 808;

record and validate the device's unique tracking, personal identification, security information 810; perform colorimetric image processing 812 that does not rely on total light intensity measurement; perform predictive analytics using the software platform 814; and finally the testing results (historical and predictive summary information) along with medical advice can be sent to users, providers, patients, caregivers, payers, insurers, etc. 816.

In process 812, the captured image is processed to calculate the concentration of each analyte based on the calibration curve of the device. The diagnostic results and/or raw data, including the image processing and diagnostic analysis done on the server side, are uploaded to a data server where the history of a patient's test results are stored for inquiry and advanced data analytics that can help to detect and prevent adverse health condition/disease.

With further reference to FIG. 8, according to an exemplary embodiment, the paper-based sensing device used in process 804 may be designed and fabricated using the workflow shown in FIG. 7 whereby diagnostic results can be generated in process 814.

Figure 9:
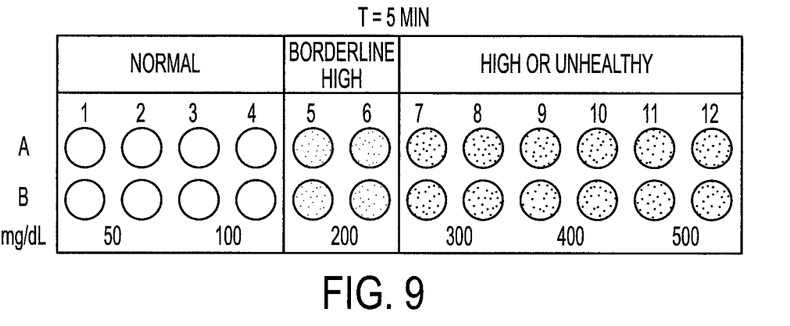
FIGS. 9, 10 and 11 illustrate Triglyceride (TG) assay testing results associated with a blood sample applied to a paper sensing device according to an exemplary embodiment of this disclosure; and, FIGS. 12, 13 and 14 illustrate total cholesterol (TC) assay testing results associated with a blood sample applied to a paper sensing device according to an exemplary embodiment of this disclosure.
Figure 10:
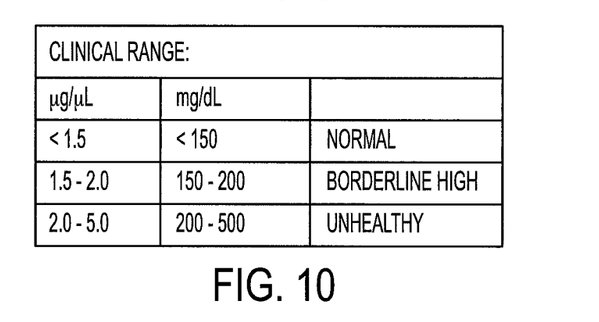
Figure 11:
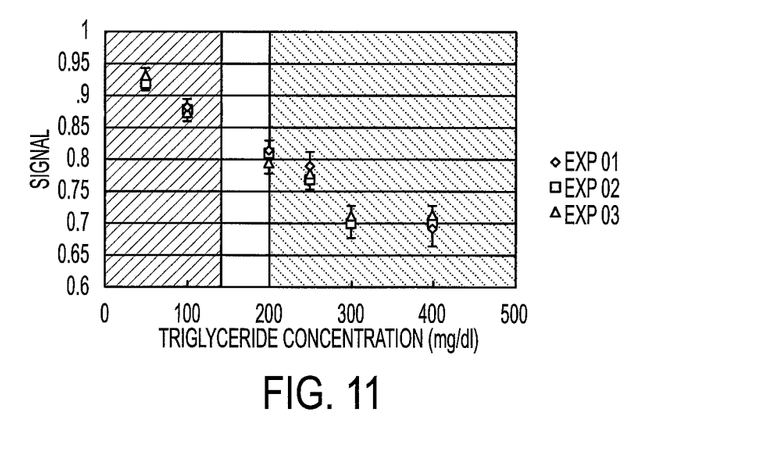

The PSAS workflow can be used to provide services associated with a lipid panel (total cholesterol, triglyceride, HDL), hemoglobin A1C and glucose multiplexing testing panel design using the paper sensing device for employees, Medicare & Medicaid wellness screening, and homecare/self-care point of care (POC) applications. FIGS. 9, 10 and 11 illustrate exemplary triglyceride testing results and references; and FIGS. 12, 13 and 14 illustrate exemplary total cholesterol assay testing results and references.

It is to be appreciated that FIG. 9 represents the reference color range after five minutes of reaction with the reagents. The reference color range corresponds to a triglyceride concentration (mg/dL). It is to be appreciated that as the triglyceride concentration increases, the color density/saturation level increases. FIG. 10 represents a clinical range reference chart displaying to a user or caregiver the normal, borderline high, and unhealthy ranges of triglyceride concentrations. The caregiver can then compare an individual's test results and place a patient's triglyceride concentration at a level corresponding to the color concentration gradient of FIG. 9 and the clinical ranges described in FIG. 10. A normal triglyceride concentration can correspond to color gradient levels 1, 2, 3, or 4. A borderline high triglyceride concentration can correspond to color gradient levels of 5 or 6. An unhealthy triglyceride concentration can correspond to color gradient levels of 7 or more (7-12). The system can store the clinical range reference chart (FIG. 10), calibration curves (FIG. 11) derived from FIG. 9 information in the database. When a patient, caregiver, or care provider submits electronic testing device data following workflow according to FIGS. 3 and 4, or FIG. 8, the system can utilize the corresponding color calibration curves and clinical ranges etc. to establish a triglyceride concentration level for this particular test. The results can then subsequently be plotted on a triglyceride sensitivity curve (FIG. 11). This new data point can be reported and also be added to the patient's historical data curve for future health-condition prediction and reference.

Figure 12:
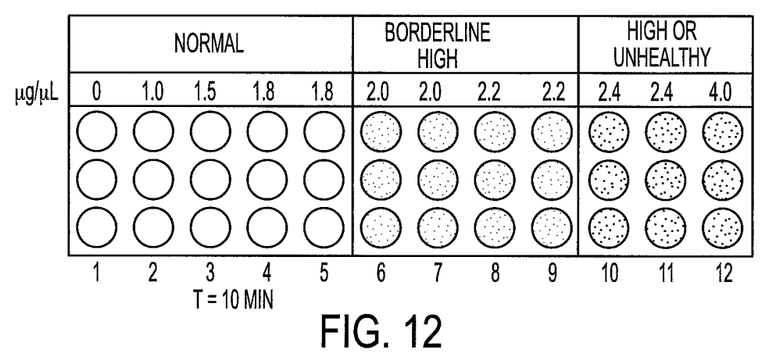
Figure 13:
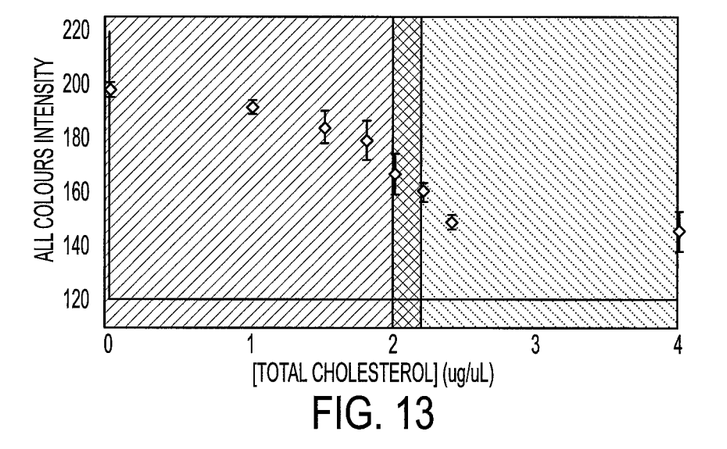

FIG. 12 represents color changes after ten minutes of reaction with the reagents and is used to create the total cholesterol calibration curve illustrated in FIG. 13. The reference color range corresponds to a total cholesterol concentration (mg/dL). It is to be appreciated that as the total cholesterol concentration increases, the color gradient increases. FIG. 12 represents a clinical range reference chart displaying to a caregiver the normal, borderline high, and unhealthy ranges of total cholesterol concentrations. The system can store the clinical range reference chart (FIG. 14), calibration curves (FIG. 13) derived from FIG. 12 information in the database. When a patient, caregiver, or a care provider submits electronic testing device data following workflow according to FIGS. 3 and 4, or FIG. 8, the system can utilize the corresponding color calibration curves and clinical ranges etc. to establish a total cholesterol concentration level for this particular test. This new data point can be reported and also be added to the patient's historical data curve for future health-condition prediction and reference.

Figure 14:
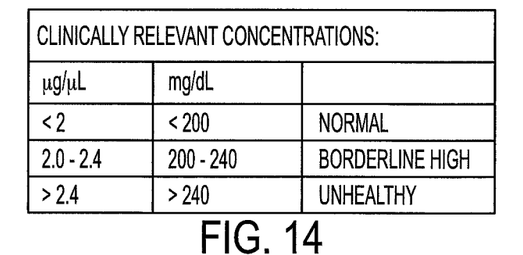

The caregiver, for example, can then compare an individual's test results and place a patient's total cholesterol concentration at a level corresponding to the color concentration gradient of FIG. 12 and the clinically relevant concentrations described in FIG. 14. A normal total cholesterol concentration can correspond to color gradient levels of 6 or less. A borderline high total cholesterol concentration can correspond to color gradient levels of 6, 7, 8, or 9. An unhealthy total cholesterol concentration can correspond to color gradient levels of 10, 11, or 12. In this manner, a caregiver can utilize the assay readout and corresponding color gradient concentration to establish a total cholesterol concentration level. The results can then subsequently be plotted on a total cholesterol sensitivity curve (FIG. 13).

Some portions of the detailed description herein are presented in terms of algorithms and symbolic representations of operations on data bits performed by conventional computer components, including a central processing unit (CPU), memory storage devices for the CPU, and connected display devices. These algorithmic descriptions and representations are the means used by those skilled in the data processing arts to most effectively convey the substance of their work to others skilled in the art. An algorithm is generally perceived as a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be understood, however, that all of these and similar terms are to be associated with the appropriate physical quantities and are merely convenient labels applied to these quantities. Unless specifically stated otherwise, as apparent from the discussion herein, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The exemplary embodiment also relates to an apparatus for performing the operations discussed herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the methods described herein. The structure for a variety of these systems is apparent from the description above. In addition, the exemplary embodiment is not described with reference to any particular programming language. It will be appreciated that a variety of programming languages may be used to implement the teachings of the exemplary embodiment as described herein.

A machine-readable medium includes any mechanism for storing or transmitting information in a form readable by a machine (e.g., a computer). For instance, a machine-readable medium includes read only memory ("ROM"); random access memory ("RAM"); magnetic disk storage media; optical storage media; flash memory devices; and electrical, optical, acoustical or other form of propagated signals (e.g., carrier waves, infrared signals, digital signals, etc.), just to mention a few examples.

The methods illustrated throughout the specification, may be implemented in a computer program product that may be executed on a computer. The computer program product may comprise a non-transitory computer-readable recording medium on which a control program is recorded, such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, or any other tangible medium from which a computer can read and use. In addition, one or more of the methods illustrated herein may be performed within a cloud based processing environment where one or more of storage and computing are performed.

Alternatively, the method may be implemented in transitory media, such as a transmittable carrier wave in which the control program is embodied as a data signal using transmission media, such as acoustic or light waves, such as those generated during radio wave and infrared data communications, and the like.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A paper-based sensor method comprising:
   in response to a test sample of a substance being applied to a paper-based sensor, the paper-based sensor reacting to the test sample to generate one or more color indicators, wherein the paper-based sensor includes a reference color thereon and a plurality of test zones each operative to display a color change by reaction of a reagent to an analyte in the test sample, wherein each test zone is associated with a different concentration of the reagent;
   at a server computer, receiving a captured image of the paper-based sensor after the test sample is applied to the paper-based sensor;
   at the server computer, processing the captured image to detect the reference color and color change on the paper-based sensor;
   at the server computer, using the color changes in the plurality of test zones, generating a calibration curve of an associated image capture device by which the image was received;
   at the server computer, determining a signal of the reference color;
   applying the signal to the calibration curve to compute a color concentration gradient of the reagent of the test sample;
   acquiring a clinical range chart from a database;
   applying the color concentration gradient to the clinical range chart to determine a total concentration level of the analyte in the test sample;
   processing one of tracking information, personal identification information, security information, color calibration information, and environmental indicators; and
   using the information, applying the total concentration to a historical curve for a patient of which the test sample is received.

2. The paper-based sensor method according to claim 1, comprising:
   communicating one or more attributes associated with the test sample to a user.

3. The paper-based sensor method according to claim 2, comprising:
   performing predictive analytics for monitoring the user's health conditions.

4. The paper-based sensor method according to claim 1, wherein the paper-based sensor includes tracking information, environmental indicators and security information, and the method validates the captured image of the paper-based sensor based on one or more of the tracking information, environmental indicators and security information.

5. The paper-based sensor method according to claim 1, wherein capturing the image of the paper-based sensor comprises a camera phone.

6. A computer program product comprising:
   a non-transitory computer-usable data carrier storing instructions that, when executed by a computer, cause the computer to perform the method of claim 1.

7. The computer program product according to claim 6, the method further comprising:
   communicating one or more attributes associated with the test sample to a user.

8. The computer program product according to claim 7, wherein the paper-based sensor includes three or more of tracking information, personal identification information, security information, color calibration information, and environmental indicators.

9. The computer program product according to claim 8, the method further comprising:
   performing predictive analytics for monitoring the user's health conditions.

10. The computer program product according to claim 9, wherein the paper-based sensor includes tracking information, environmental indicators and security information, and the method validates the captured image of the paper-based sensor based on one or more of the tracking information, environmental indicators and security information.

11. A paper-based sensor processing system comprising:
a paper-based sensor, including a reference color thereon and a plurality of test zones each operative to display a color change by reaction of a reagent to an analyte in a test sample being applied to the paper-based sensor, wherein each test zone is associated with a different concentration of the reagent;
a server computer configured to: receive an image of the paper-based sensor at a server computer after the test sample is applied to the paper-based sensor;
process the captured image to detect the reference color and color change on the paper-based sensor;
use the color changes in the plurality of test zones, to generate a calibration curve of an associated image capture device by which the image was received;
determine a signal of the reference color;
apply the signal to the calibration curve to compute a color concentration gradient of the reagent of the test sample;
acquire a clinical range reference chart from a database; and
apply the color concentration gradient to the clinical range reference chart to determine a total concentration level of the analyte in the test sample.

12. The paper-based sensor processing system according to claim 11, wherein the system stores the clinical range reference chart.

13. The paper-based sensor processing system according to claim 12, wherein the system stores the clinical range reference chart to compare to the one or more attributes associated with the test sample.

14. The paper-based sensor processing system according to claim 13, wherein the color gradient level is plotted on a calibration curve and is added to a patient's historical data curve for future health condition prediction.

15. The paper-based sensor processing system according to claim 14, wherein the paper-based sensor includes three or more of tracking information, personal identification information, security information, color calibration information, and environmental indicators.

16. The paper-based sensor processing system according to claim 15, wherein further comprising:
wherein the server computer is further configured to:
perform predictive analytics for monitoring the user's health conditions.

* * * * *